United States Patent

Mirajkar et al.

[11] Patent Number: 6,113,884
[45] Date of Patent: Sep. 5, 2000

[54] MIXED SURFACTANT, HIGH FOAMING DENTIFRICE EXHIBITING ENHANCED ANTIBACTERIAL COMPOUND UPTAKE ON DENTAL TISSUE

[75] Inventors: Yelloji-Rao K. Mirajkar, Piscataway; Nuran Nabi, Cranbury; John Afflitto, Brookside; Abdul Gaffar, Princeton, all of N.J.

[73] Assignee: Colgate-Palmolive Company, New York, N.Y.

[21] Appl. No.: 09/192,255

[22] Filed: Nov. 13, 1998

[51] Int. Cl.⁷ .................. A61K 7/16; A61K 7/18
[52] U.S. Cl. .................................. 424/49; 424/52
[58] Field of Search ........................... 424/49–88

[56] References Cited

U.S. PATENT DOCUMENTS

| | | |
|---|---|---|
| 5,188,821 | 2/1993 | Gaffer et al. . |
| 5,192,531 | 3/1993 | Gaffar et al. . |
| 5,256,401 | 10/1993 | Duckenfield et al. ............ 424/49 |
| 5,292,502 | 3/1994 | Burke et al. .................... 424/49 |
| 5,296,215 | 3/1994 | Burke et al. .................... 424/49 |
| 5,368,844 | 11/1994 | Gaffar et al. . |
| 5,449,763 | 9/1995 | Wulff et al. .................... 536/18.6 |
| 5,470,561 | 11/1995 | Klugkist et al. . |
| 5,605,676 | 2/1997 | Gaffar et al. .................. 424/49 |
| 5,628,985 | 5/1997 | Stiller et al. ................... 424/49 |
| 5,630,999 | 5/1997 | Burke et al .................... 424/49 |
| 5,635,469 | 6/1997 | Fowler et al. ................... 570/406 |
| 5,661,189 | 8/1997 | Grieveson et al. .............. 514/784 |
| 5,690,911 | 11/1997 | Mirajkar et al. . |
| 5,723,500 | 3/1998 | Stringer et al. . |
| 5,734,029 | 3/1998 | Wulff et al ..................... 536/4.1 |
| 5,833,956 | 11/1998 | Gorlin et al. . |
| 5,843,406 | 12/1998 | Mordarski et al. .............. 424/49 |
| 5,929,024 | 7/1999 | Stringer et al. ................. 510/504 |

*Primary Examiner*—Shep K. Rose
*Attorney, Agent, or Firm*—Henry S. Goldfine; Paul Shapiro

[57] ABSTRACT

A high foaming oral composition comprising in an orally acceptable vehicle, an effective antiplaque, antibacterial compound, and at least about 2% by weight of a mixed anionic/nonionic surfactant system in a weight ratio of about 7:1 to 2:1, respectively, which ratios are effective to increase the uptake of the antibacterial compound to dental tissue so as to enhance the therapeutic efficacy of the administered antibacterial compound.

26 Claims, No Drawings

MIXED SURFACTANT, HIGH FOAMING DENTIFRICE EXHIBITING ENHANCED ANTIBACTERIAL COMPOUND UPTAKE ON DENTAL TISSUE

BACKGROUND OF THE INVENTION

1. Field of the Invention

The present invention relates to high foaming oral compositions containing an antibacterial compound for the inhibition of bacterial plaque accumulation on dental tissue and more particularly to such compositions containing an antibacterial compound and a mixed anionic/nonionic surfactant system which promotes significantly higher uptake of the antibacterial compound on dental tissue.

2. The Prior Art

Dental plaque is a soft deposit which forms on teeth and is comprised of an accumulation of bacteria and bacterial by-products. Plaque adheres tenaciously at the points of irregularity or discontinuity, e.g., on rough calculus surfaces, at the gum line and the like. Besides being unsightly, plaque is implicated in the occurrence of gingivitis and other forms of periodontal disease.

A wide variety of antibacterial agents have been suggested in the art to retard plaque formation and the oral infections and dental disease associated with plaque formation. For example, halogenated hydroxydiphenyl ether compounds such as triclosan are well known to the art for their antibacterial activity and have been used in oral compositions to counter plaque formation by bacterial accumulation in the oral cavity. The effectiveness of the antibacterial agent is dependent upon its delivery to and uptake by teeth and soft tissue areas of the gums.

Surfactants, and particularly anionic surfactants, such as sodium lauryl sulfate (SLS) are conventionally included in oral formulations, to provide solubilization, dispersion, emulsification and wetting of the other ingredients present, especially flavor oils. Further, surfactants provide a cosmetic effect in promoting the foaming of the oral composition. Oral compositions with strong foaming ability are preferred by consumers, since it is perceived that the greater the foaming, the better the composition cleans the tooth and other oral surfaces, removing stain, plaque and debris therefrom.

U.S. Pat. No. 5,690,911 discloses an oral composition containing an antiplaque halogenated diphenyl ether or phenolic antibacterial agent and a mixed anionic/nonionic surfactant system at a weight ratio of about 14:1 to 9:1 anionic to nonionic surfactant; wherein, the uptake of the antibacterial agent to the dental tissue is increased to enhance the therapeutic efficacy of the administered antibacterial agent. Further, U.S. Pat. No. 5,690,911 further discloses that increasing the ratio of nonionic surfactant will lead to an unacceptable consumer taste. The working examples of U.S. Pat. No. 5,690,911 demonstrate that the optimum uptake of antibacterial agent occurs at approximately a 9:1 anionic to nonionic surfactant weight ratio, when the total amount of surfactant present in the oral composition ranges from about 1.3 to about 1.5% by weight. Unexpectedly, as will be demonstrated below, as the total level of surfactant is increased from 1.5% by weight to about 3.0%, the optimum uptake of antibacterial agent occurs at a significantly lower anionic to nonionic ratio.

There is a need in the art to provide means whereby the delivery to and uptake by dental tissue of antibacterial compounds may be increased to further to enhance the therapeutic efficacy of the antibacterial agent.

SUMMARY OF THE INVENTION

In accordance with this invention there is provided an oral composition comprising in an orally acceptable vehicle, an effective antiplaque amount of an halogenated diphenyl ether or phenolic antibacterial compound, and at least about 2% by weight of a mixed anionic/nonionic surfactant system present at weight ratios of from about 7:1 to about 2:1 anionic to nonionic surfactant; whereby, the delivery and uptake of the antibacterial compound to oral surfaces is increased to effect enhanced therapeutic efficacy of the administered compound.

Unexpectedly, as will hereinafter be demonstrated, oral compositions containing approximately 0.4 to 0.5%, but less than about 1.0% nonionic surfactant, and having a weight ratio of about 4:1 anionic/nonionic surfactant, provide a consumer acceptable taste.

DETAILED DESCRIPTION OF THE PREFERRED EMBODIMENTS

The term "oral composition" is used herein to designate products which, in the ordinary course of usage, are retained in the oral cavity for a time sufficient to contact substantially all of the dental surfaces but are not intentionally ingested. Such products include, for example, dentifrices such as toothpaste, gels and toothpowders; liquid toothpaste; and mouthwashes.

It is essential and critical that the antibacterial containing oral composition of the present high foaming invention contain a mixed anionic/nonionic surfactant system; wherein, the anionic surfactant is the major constituent, the weight ratio of the anionic surfactant to nonionic surfactant being about 7:1 to 2:1 respectively, with the optimum being approximately 4:1. The anionic/nonionic surfactant mixture of the present invention is found to enhance uptake of halogenated diphenyl ether and phenolic antibacterial compounds on dental tissue when the surfactant mixture is incorporated in the oral composition in amounts effective to achieve high foaming, such amounts greater than 2% by weight, preferably at least about 2.5% and most preferably at least about 3.0% by weight of the oral composition. Increasing the nonionic surfactant in the surfactant mixture to an amount resulting in an anionic to nonionic surfactant weight ratio of less than about 2:1, e.g. 1:1, wherein the nonionic would be of the order of about 1.0% or more by weight of the oral composition, produces an unsatisfactory taste which is unacceptable to consumers.

Halogenated diphenyl ether antibacterial compounds useful for the preparation of the oral care compositions of the present invention particularly desirable from considerations of antiplaque effectiveness and safety include 2,4,4'-trichloro-2'-hydroxy-diphenyl ether (triclosan) and 2,2'-dihydroxy-5,5'-dibromo-diphenyl ether.

Phenolic compounds useful in the practice of the present invention include phenol and its homologs, mono and polyalkyl and aromatic halophenols, resorcinol and its derivatives and bisphenolic compounds, such phenolic compounds being more fully disclosed in U.S. Pat. No. 5,368,844. Preferred phenolic compounds are n-hexyl resorcinol and 2,2'-methylene bis (4-chloro-6-bromophenol).

The halogenated diphenyl ether or phenolic antibacterial compound is present in the oral composition of the present invention in an effective antiplaque amount, typically about 0.05% to about 2.0% by weight, and preferably about 0.1% to about 1% by weight of the oral composition.

Anionic surfactants useful in the practice of the present invention include long chain fatty or poly-lower alkoxy groups plus hydrophilic radicals. They will usually be in the form of salts, especially water soluble salts of alkali metals. Useful anionic surfactants include the higher fatty acid monoglyceride monosulfates, such as the sodium salts of the monosulfated monoglycerides of hydrogenated coconut oil fatty acid; higher alkyl sulfates, such as sodium lauryl sulfate; higher alkyl aryl sulfonates, such as sodium linear dodecyl benzene sulfonate; higher olefin sulfonates, such as sodium higher olefin sulfonate in which the olefin group is 12 to 21 carbon atoms; higher alkyl alkali sulfoacetates such as sodium lauryl sulfoacetate; higher fatty acid esters of 1,2-dihydroxypropane sulfonates; the substantially saturated higher aliphatic acyl amides of lower aliphatic aminocarboxylic acid alkali metal salts, such as those having 12 to 16 carbon atoms in the fatty acyl radicals; higher alkyl polylower alkoxy (of 10 to 100 alkoxies) sodium sulfates; higher fatty acid sodium and potassium soaps of coconut oil and tallow, and the like. The anionic surfactant, sodium lauryl sulfate, is preferred in the practice of the present invention.

Nonionic surfactants useful in the practice of the present invention include a nonionic water soluble polyoxyethylene monoester of sorbitol with a $C_{10-18}$ fatty acid ester of sorbitol consisting predominantly of the monoester, condensed with about 20–100, preferably about 20 to about 60, moles of ethylene oxide. The fatty acid (aliphatic hydrocarbon-monocarboxylic acid) may be a saturated or unsaturated acid such as lauric palmitic, stearic, oleic acid. Polyoxyethylene sorbitan fatty esters, sold under the trademark Tween are a preferred class of nonionic surfactants. Tween 20® and Tween 60® are especially preferred, which are a polyoxyethylene (20) and a polyoxyethylene (60) sorbitan monolaurate commercially available from ICI. Another preferred class of nonionic surfactants include polyoxyethylene polyoxypropylene block copolymers having the formula $HO(C_2H_4O)b(C_3H_6O)a(C_2H_4O)bH$ wherein a is an integer such that the hydrophobic base represented by $(C_3H_6)$ has a molecular weight of about 2750 to 4,000, b is an integer such that the hydrophilic moiety represented by $(C_2H_4O)$ constitutes about 70–80% by weight of the copolymer. Block copolymers of this composition are available commercially from BASF under the trademark Pluronic F type.

Pluronic F-77, which has a molecular weight of 6,600 and contains 70% of the hydrophilic polyoxyethylene moiety, and Pluronic F-127, which has a molecular weight of 12,600 and contains 70% of the hydrophilic polyoxyethylene moiety, are preferred in the practice of the present invention.

Other nonionic surfactants useful in the preparation of the compositions of the present invention include polyethoxylated glycerol containing six to seven ethoxy groups having a molecular weight of about 400 available under the trademark Findet from Kao Company, polyethoxylated castor oil available from BASF Company under the trademark Cremaphor and alkyl glucosides produced by reacting glucose or an oligosaccharide with a fatty alcohol containing 12–22 carbon atoms and more preferably with alcohols containing an alkyl group having 12 to 18 carbon atoms. Polyglucosides containing C12–C16 alkyl glucosides are available commercially from Horizon Chemical Division of Henkel, Inc. under the trademark Plantaren.

In the preparation of an oral composition in accordance with the practice of the present invention, an orally acceptable vehicle including a water-phase with humectant is present. The humectant is preferably glycerine, sorbitol, and/or propylene glycol. Water is present typically in amount of at least about 10% by weight, generally about 30 to 60% by weight and the humectant concentration typically totals about 40–60% by weight of the oral composition.

Dentifrice compositions such as toothpastes and gels also typically contain polishing materials including crystalline silica, having a particle size of up to about 20 microns, such as commercially available Zeodent 115, silica gel or colloidal silica, complex amorphous alkali metal aluminosilicates, calcined alumina, hydrated alumina, sodium metaphosphate as well as sodium bicarbonate, calcium carbonate, calcium pyrophosphate, dicalcium phosphate and dicalcium phosphate dihydrate. Typically, the polishing material is included in semi-solid or pasty dentifrice compositions of the present invention in an amount of from about 15 to about 60% by weight and preferably from about 20 to about 55%.

Pyrophosphate salts having antitartar efficacy such as a dialkali or tetraalkali metal phosphate salts such as $Na_4P_2O_7$, $K_4P_2O_7$, $Na_2K_2P_2O_7$, $Na_2H_2P_2O_7$ and $K_2H_2P_2O_7$, long chain polyphosphates such as sodium hexametaphosphate and cyclic phosphate such as sodium trimetaphosphate may be incorporated in oral compositions of the present invention preferably at concentration of about 0.5 to about 8.0% by weight and preferably about 0.5 to about 3.0% by weight. In liquid oral preparations, the pyrophosphate salts are incorporated at a concentration of about 0.1 to about 2% by weight.

Dentifrices prepared in accordance with the present invention typically contain a natural or synthetic thickener in proportions of about 0.1 to about 5% by weight, preferably about 0.5 to about 2% by weight. Suitable thickeners include Irish moss (Viscarin), i-carrageenan, gum tragacanth, starch, polyvinylpyrrolidone, hydroxyethypropyl cellulose, hydroxybutyl methyl cellulose, hydroxypropyl methylcellulose, hydroxyethyl cellulose, sodium carboxymethyl cellulose and colloidal silica.

The oral composition may also contain a source of fluoride ions, or fluoride-providing compound, as an anticaries agent, in an amount sufficient to supply about 25 ppm to 5,000 ppm of fluoride ions and preferably 500 to 1500 ppm fluoride ions. Among these compounds are inorganic fluoride salts, such as soluble alkali metal salts, for example, sodium fluoride, potassium fluoride, sodium fluorosilicate, ammonium fluorosilicate and sodium monofluorphosphate, as well as tin fluorides, such as stannous fluoride and stannous chloride.

An antibacterial enhancing agent may also be included in the oral composition. The use of antibacterial enhancing agents in combination with antibacterial agents such as triclosan is known to the art, as for example U.S. Pat. No. 5,188,821 and U.S. Pat. No. 5,192,531. Preferably, the antibacterial enhancing agent is an anionic polymeric polycarboxylate having a molecular weight of about 1,000 to about 1,000,000, preferably about 30,000 to about 500,000. Anionic polymeric polycarboxylates are generally employed in the form of their free acids or preferably as a partially or fully neutralized water soluble alkali metal salt, e.g., sodium, potassium or ammonium salts. Preferred antibacterial enhancing agents are 1:4 to 4:1 copolymers of maleic anhydride or acid with another polymerizable ethylenically unsaturated monomer, preferably a methyl vinyl ether/maleic anhydride copolymer having a molecular weight (M.W.) of about 30,000 to abut 1,000,000, most preferably about 30,000 to about 500,000. These copolymers are available, for example, under the trademark Gantrez, e.g., Gantrez AN 139 (M.W. 500,000), AN 119 (M.W. 250,000); and preferably Gantrez S-97 Pharmaceutical Grade (M.W. 700,000), of GAF Corporation.

The antibacterial enhancing agent is incorporated in the compositions of the present invention in weight amounts of about 0.05 to about 3%, and preferably about 0.1 to about 2%.

Any suitable flavoring or sweetening material may also be employed in the preparation of the oral compositions of the present invention. Examples of suitable flavoring constituents include flavoring oils, e.g. oil of spearmint, peppermint, wintergreen, clove, sage, eucalyptus, marjoram, cinnamon, lemon, orange, and methyl salicylate. Suitable sweetening agents include sucrose, lactose, maltose, xylitol, sodium cyclamate, aspartyl phenyl alanine methyl ester, saccharine and the like. Suitably, flavor and sweetening agents may each or together comprise from about 0.1% to 5% more of the oral composition.

Various other materials may be incorporated in the oral preparations of this invention such as whitening agents, including urea peroxide, calcium peroxide, and hydrogen peroxide, preservatives, vitamins such as vitamin B6, B12, E and K, silicones, chlorophyll compounds and potassium salts for the treatment of dental hypersensitivity such as potassium nitrate and potassium citrate. These agents, when present, are incorporated in the compositions of the present invention in amounts which do not substantially adversely affect the properties and characteristics desired.

The manufacture of the oral composition of the present invention is accomplished by any of the various standard techniques for producing such compositions. More specifically, to prepare a toothpaste of the present invention, generally small amounts of any organic thickeners, such as carboxymethyl cellulose (CMC) or xanthan gum are added along with the humectants e.g. glycerin, sorbitol, propylene glycol, polypropylene glycol, and polyethylene glycol in a conventional mixer (the gel tank) under agitation and with such organic thickeners as carrageenan. After these ingredients are dissolved, water is added to the mixer with continuing agitation. Into the mixer are added sweeteners; any active ingredients, such as fluoride ion releasing salts, e.g. sodium fluoride; any efficacy enhancing agents, such as anionic polycarboxylate; and less quantity (i.e. minor) ingredients, including any pigment, such as $TiO_2$, or preservatives, such as methyl or propyl paraben. As the resultant mixture is agitated, the any inorganic thickener, such as a silica thickening agent is added until a homogeneous gel phase is formed.

The gel phase mixture is then transferred to a high speed/vacuum mixer (the vacuum mixer); whereupon any abrasive material is added and the mixture is agitated under vacuum of about 25 to about 30 inches of Hg, for about 20 minutes. Any water insoluble antibacterial agent, such as triclosan, is dissolved in the flavor oils and added with the surfactant to the mixture, which mixture is mixed at high speed for at least 10 minutes, preferably 15 to 20 minutes, under vacuum of from about 25 to 30 inches of Hg, preferably about 28 inches Hg. The resultant product is a homogeneous, semi-solid, extrudable, thixotropic paste.

The following examples are further illustrative of the present invention, but it is understood that the invention is not limited thereto. All amounts and proportions referred to herein and in the appended claims are by weight, unless otherwise indicated.

EXAMPLE I

The effect of a mixture of anionic and nonionic surfactants when present in an oral composition on the uptake absorption to dental tissue of a halogenated diphenyl ether antibacterial agent was assessed using disks of saliva coated hydroxyapatite (SCHAP), the mineral phase of dental enamel, as an in vitro experimental model for human teeth. The in vitro assessment has been found to be correlatable to in vivo uptake of antibacterial agents on dental tissue surfaces.

In this in vitro assessment, hydroxyapatite (HAP) is washed extensively with distilled water, collected by vacuum filtration, and dried overnight at 37° C. The dried HAP is ground into a powder and 150 milligrams (mgs) of the powder is placed into a chamber of a KBr pellet die (Barnes Analytical, Stanford, Conn.). The HAP powder is compressed for 6 minutes at 10,000 pound in a Carver Laboratory press to prepare 13 mm diameter disks which are sintered for 4 hours at 800° C. in a Thermolyne furnace.

To determine the delivery and uptake to dental surfaces of a triclosan dentifrice of the present invention, identified as Composition A in Table I below, SCHAP disks were treated with a slurry of this dentifrice containing 0.2% by weight triclosan and 2.5% of a surfactant mixture comprised of a 4:1 weight ratio of anionic surfactant (sodium lauryl sulphate) to nonionic surfactant (Pluronic F 127). The amounts of dentifrice slurry used to contact the disks simulated in vivo surface to volume ratios found in the mouth. The dentifrice slurries were an aqueous slurry which contained all the components of a dentifrice. The aqueous slurry, in part, simulates the brushing condition. After incubation for 30 minutes at 37° C., the SCHAP disks were removed from the dentifrice slurry, washed three times with water.

The mean uptake absorption of triclosan, on SCHAP disks, from Composition A is set forth in Table II below.

For purposes of comparison, the procedure of Example I was repeated twice, once with dentifrice containing a 9:1 anionic surfactant to nonionic surfactant weight ratio, designated "Composition B" in Table I, and once with a dentifrice containing no nonionic surfactant, designated "Composition C" in Table I. The uptake and retention of triclosan from comparative Compositions B and C is also set forth in Table II below.

TABLE I

Compositions Tested

| Composition: Ingredients | A Wt. % | B Wt. % | C Wt. % |
| --- | --- | --- | --- |
| Glycerin | 1.00 | 1.00 | 1.00 |
| Sorbitol (70%) | 27.00 | 27.00 | 27.00 |
| Viscarin | 0.52 | 0.52 | 0.52 |
| CMC 7 MF | 0.78 | 0.78 | 0.78 |
| Sodium Saccharin | 0.30 | 0.30 | 0.30 |
| Sodium MFP | 1.14 | 1.14 | 1.14 |
| Sodium Bicarbonate | 0.50 | 0.50 | 0.50 |
| N-Sodium Silicate | 0.80 | 0.80 | 0.80 |
| Deionized Water | 28.19 | 28.47 | 28.69 |
| Methyl Paraben | 0.10 | 0.10 | 0.10 |
| Propyl Paraben | 0.02 | 0.02 | 0.02 |
| Triclosan | 0.20 | 0.20 | 0.20 |
| Flavor Oils | 0.95 | 0.95 | 0.95 |
| PPC | 36.00 | 36.00 | 36.00 |
| Pluronic F 127 | 0.5 | 0.22 | 0.0 |
| SLS | 2.00 | 2.00 | 2.00 |
| Total | 100.00 | 100.00 | 100.00 |

TABLE II

Uptake of Triclosan on SCHAP Disks

| Composition | Triclosan Uptake (ppm) | SD* | % Increase Compared to Composition C |
| --- | --- | --- | --- |
| A | 68.61 | 5.19 | 32.78 |
| B | 57.48 | 3.29 | 11.24 |
| C | 51.67 | 14.34 | — |

*Standard deviation ±

The results recorded in Table II show that uptake of triclosan on SCHAP disks from Composition A is significantly enhanced, by about 32.8%, by the presence in the dentifrice of a mixture of anionic (SLS) and nonionic surfactants at a weight ratio of 4:1 as compared to Composition C in which the anionic surfactant (SLS) was the sole surfactant. In comparison, Composition B wherein the anionic to nonionic surfactant ratio was 9:1 by weight, showed no statistically significant enhancement over comparative Composition C in which the anionic surfactant (SLS) was the sole surfactant.

EXAMPLE II

An inhibition of bacterial growth study was performed to demonstrate the adsorption of the antibacterial agent of a dentifrice of the present invention onto SCHAP disks and the resulting inhibition of bacterial growth using such disks. SCHAP (hydroxyapatite) disks which were saliva coated (after overnight incubation with clarified saliva at 37° C.) were incubated at 37° C. for 30 minutes with 1 ml supernatant of 1:1 slurry of a dentifrice of the present invention, Composition A, and water. After the incubation, the dentifrice was aspirated, the disks were transferred into a falcon tube, washed three times with 5 ml water, vertexed and aspirated. The disks were then inoculated with 10 ml bacterial suspension containing Actinomyces viscosus, a bacteria associated with dental caries, at a concentration of 0.5 OD (Optical Density) at 610 nm. The growth of bacteria was then measured after 24 hours in terms of OD, wherein the lower the OD, the lower the presence of bacteria, i.e. the lower the growth of bacteria. The mean OD result obtained is recorded in Table III, below.

For comparison, the inhibition of bacterial growth procedure of Example II was repeated with comparative Compositions B and C. The growth of bacteria was assessed as OD and the mean results are recorded in Table III, below.

TABLE III

Inhibition of Bacterial Growth

| Composition | Ratio Anionic to Nonionic Surfactant | OD at 610 nm | % Reduction In Growth vs. Composition C |
|---|---|---|---|
| A | 4:1 | 0.82 | 20.4% |
| B | 9:1 | 0.95 | 7.8% |
| C | 100:0 | 1.03 | — |

The results recorded in Table III show that the bacterial inhibition of the antibacterial agent adsorbed by SCHAP disks incubated in Composition A, containing a 4:1 anionic to nonionic surfactant mixture of the present invention, is significantly more efficacious than SCHAP disks incubated in a 9:1 weight ratio (Composition B). Further, when compared to SCHAP disks incubated in a dentifrice containing an equivalent amount of only anionic (Composition C) as the sole surfactant, the SCHAP disks incubated in Composition A provided over 20% greater inhibition of bacterial growth.

EXAMPLE III

The foaming ability of a high concentration, i.e. 2.5% by weight aqueous surfactant solution, the surfactant level of the present invention, was assessed using an inverted cylinder foam test method. Twenty milliliters (ml) of a 2.5% by weight aqueous surfactant solution containing a 4:1 SLS, to Pluronic F-127 surfactant mixture, designated Composition D, was poured into a 100 ml graduated cylinder. Under ambient room conditions of temperature and pressure, the 100 ml graduated cylinder was then inverted and righted 40 times and the resulting total ml level of solution and foam recorded in Table IV, below.

For comparison, the foaming ability of a 1.5% by weight concentration of a 4:1 SLS to Pluronic F-127 aqueous surfactant solution, designated Composition E, was assessed using the procedure of Example III and the result also recorded in Table IV.

TABLE IV

Foaming Ability at Higher Surfactant Level

| Composition | Level of Solution & Foam | % Increase |
|---|---|---|
| D | 96 | 26.3% |
| E | 76 | — |

Referring to Table IV, Composition D with a 2.5% by weight concentration of total surfactants provided a significantly greater level of foam than Composition E with a 1.5% by weight concentration of total surfactants.

EXAMPLE IV

The taste of an antibacterial dentifrice composition of the present invention, designated Composition F, was assessed by a test panel. The formulation of Composition F and the panel's taste test results are shown in Table V, below.

For comparison, an antibacterial dentifrice composition, designated Composition G, was formulated with the level of nonionic surfactant being 1% by weight, and subjected to the same panel taste test of Example IV. The formulation of comparative Composition G and the panel's taste test results are also shown in Table V, below.

TABLE V

Taste Test

| Ingredient | Composition F (Weight %) | Composition G (Weight %) |
|---|---|---|
| Glycerin | 15.0 | 15.0 |
| Viscarin | 0.65 | 0.65 |
| Sodium Saccharin | 0.15 | 0.15 |
| Sorbitol (70% Solution) | 10.0 | 10.0 |
| Pluronic F-127 | 0.5 | 1.0 |
| Deionized Water | 20.69 | 20.19 |
| Dicalcium Phosphate | 13.0 | 13.0 |
| Calcium Carbonate | 36.5 | 36.5 |
| Triclosan | 0.2 | 0.2 |
| Flavor Oils | 1.0 | 1.0 |
| SLS | 2.31 | 2.31 |
| Total Ingredients | 100.0 | 100.0 |
| Result of Panel Taste Test | Acceptable | Not Acceptable |

Referring to Table V above, the panel test rated Composition F of the present invention as "Acceptable" in terms of taste and comparative Composition G, which exhibited a strong bitter type taste as "Not Acceptable".

What is claimed is:

1. A high foaming oral composition exhibiting increased uptake by dental tissue of antibacterial compounds contained therein, the composition comprising in an orally acceptable vehicle an effective therapeutic amount of a halogenated diphenyl ether or phenolic antibacterial compound and a mixture of an anionic and a nonionic surfactants at a weight ratio of about 7:1 to about 2:1; wherein the mixture of anionic and nonionic surfactants is at least 2% by weight of the oral composition.

2. The composition of claim 1 wherein the antibacterial agent is incorporated in the composition at a concentration of about 0.05 to about 2.0% by weight.

3. The composition of claim 1 wherein the antibacterial agent is triclosan.

4. The composition of claim 1 wherein the surfactant mixture is present in the composition at a concentration of about 3.0% by weight.

5. The composition of claim 1 wherein the anionic surfactant is sodium lauryl sulfate.

6. The composite of claim 1 wherein the nonionic surfactant is a polyoxyethylene polyoxypropylene block copolymer.

7. The composition of claim 1 wherein the nonionic surfactant is a polyethoxylated castor oil.

8. The composition of claim 1 wherein the nonionic surfactant is a polyoxyethylene sorbital fatty ester.

9. The composition of claim 1 wherein the nonionic surfactant is polyethoxylated glycerol.

10. The composition of claim 1 wherein the nonionic surfactant is an alkyl glucoside.

11. The composition of claim 1 wherein an anionic polymeric polycarboxylate is present in the composition.

12. The composition of claim 11 wherein the anionic polymeric polycarboxylate is a methyl vinyl ether/maleic anhydride copolymer.

13. The composition of claim 1, wherein the nonionic surfactant is less than about 1.0% by weight of the composition.

14. A method for the treatment and prevention of bacterial plaque accumulation on teeth which comprises administering to the oral cavity a high foaming oral composition comprising an orally acceptable vehicle containing an effective therapeutic amount of a halogenated diphenyl ether or phenolic antibacterial compound and a mixture of anionic and nonionic surfactants at a weight ratio of about 7:1 to about 2:1, wherein the mixture of anionic and nonionic surfactants is at least 2% by weight of the oral composition, the antibacterial compound exhibiting increased uptake to dental tissue.

15. The method of claim 14 wherein the antibacterial agent is incorporated in the composition at a concentration of about 0.05 to about 2.0% by weight.

16. The method of claim 14 wherein the antibacterial agent is triclosan.

17. The method of claim 14 wherein the surfactant mixture incorporated in the composition at a concentration of about 3.0% by weight.

18. The method of claim 14 wherein the anionic surfactant is sodium lauryl sulfate.

19. The method of claim 14 wherein the nonionic surfactant is a polyoxyethylene polyoxypropylene block copolymer.

20. The method of claim 14 wherein the nonionic surfactant is a polyethoxylated castor oil.

21. The method of claim 14 wherein the nonionic surfactant is a polyoxyethylene sorbitan fatty ester.

22. The method of claim 14 wherein the nonionic surfactant is polyethoxylated glycerol.

23. The method of claim 14 wherein the nonionic surfactant is an alkyl polyglucoside.

24. The method of claim 14 wherein an anionic polymeric polycarboxylate is present in the vehicle.

25. The method of claim 24 wherein the anionic polymeric polycarboxylate is a methyl vinyl ether/maleic anhydride copolymer.

26. The method of claim 14 wherein the nonionic surfactant is less than about 1.0% by weight.

* * * * *